United States Patent
Pitts Crick et al.

[11] Patent Number: 6,104,949
[45] Date of Patent: Aug. 15, 2000

[54] MEDICAL DEVICE

[75] Inventors: Jonathan Pitts Crick, Bristol, United Kingdom; Geeske Van Oort, Nieuwleusen, Netherlands

[73] Assignee: Vitatron Medical, B.V., Dieren, Netherlands

[21] Appl. No.: 09/150,014

[22] Filed: Sep. 9, 1998

[51] Int. Cl.$^7$ .................................................. A61B 5/05
[52] U.S. Cl. .............................................. 600/547; 607/9
[58] Field of Search ................................. 600/547, 506, 600/536; 324/600; 607/8, 9

[56] References Cited

U.S. PATENT DOCUMENTS

| | | | |
|---|---|---|---|
| 4,899,758 | 2/1990 | Finkelstein et al. | 128/672 |
| 5,040,536 | 8/1991 | Riff | 128/419 PG |
| 5,178,151 | 1/1993 | Sackner | 128/672 |
| 5,213,098 | 5/1993 | Bennett et al. | 128/419 PG |
| 5,233,984 | 8/1993 | Thompson | 607/18 |
| 5,263,491 | 11/1993 | Thornton | 128/774 |
| 5,409,009 | 4/1995 | Olson | 128/661.08 |
| 5,417,717 | 5/1995 | Salo et al. | 607/18 |
| 5,441,524 | 8/1995 | Rueter et al. | 607/18 |
| 5,562,711 | 10/1996 | Yerich et al. | 607/17 |
| 5,634,467 | 6/1997 | Nevo | 128/672 |
| 5,730,122 | 3/1998 | Lurie | 128/207.12 |
| 6,016,445 | 1/2000 | Baura | 600/547 |
| 6,044,294 | 3/2000 | Mortazavi et al. | 600/547 |

FOREIGN PATENT DOCUMENTS

WO 98/02209  1/1998  WIPO .......................... A61N 1/375

*Primary Examiner*—Marvin M. Lateef
*Assistant Examiner*—Eleni Mantis Mercader
*Attorney, Agent, or Firm*—Thomas F. Woods; Michael J. Jaro; Harold Patton

[57] ABSTRACT

A device and method useful in the diagnosis and treatment of congestive heart failure. Specifically the present invention senses the trans-thoracic impedance as well as patient posture. By correlating changes in posture with trans-thoracic impedance changes, the present invention is able to diagnose and assess the degree of congestive heart failure. The present invention is described in the context of an implantable pulse generator system, but it may also be practiced in conjunction with various types of implantable devices.

19 Claims, 6 Drawing Sheets

MEDICAL DEVICE

FIELD OF THE INVENTION

The present invention relates generally to medical devices, and more particularly, to a method and device for the diagnosis or treatment of congestive heart failure.

BACKGROUND OF THE INVENTION

Heart failure is a condition which affects thousands of people throughout the world. Put into the most simple terms, congestive heart failure is the inability of the heart to pump blood at an adequate rate in response to the filling pressure. Such a condition can have many consequences, including congestion in the tissues, peripheral as well as pulmonary edema, and shortness of breath. In its most severe stages, congestive heart failure results in death.

For this reason, many attempts to treat heart failure have been tried. These past attempts include both electrical stimulation as well as drug therapy or both in combination. See for example, Bennett et al. U.S. Pat. No. 5,213,098 (electrical stimulation) or Kramer U.S. Pat. No. 5,405,362, White U.S. Pat. No. 4,360,031, Ellinwood U.S. Pat. Nos. 3,923,060 or 4,003,379 (electrical stimulation and drug therapy)

To date drug therapy is the method of treatment which has enjoyed the greatest success. Such drug therapies include, for example, diuretic agents and angiotensin converting enzyme inhibitors. One particular method which has been found to be somewhat effective in reducing the symptoms of heart failure is intermittent use of nitroglycerin to the body.

Although various drug therapies may be effective in select patients, often such a treatment in many cases has limited effectiveness or is difficult to administer or both. For example, nitroglycerin is only effective if administered at the right time and therefor usually requires physician supervision and can lead to a number of side effects including hypotension.

Thus it would be desirable to provide a way to detect and quantitatively monitor the degree of congestive heart failure. Such quantitative monitor should be sensitive to early changes of heart failure and both easy and convenient to use, and require little or no physician supervision. It is a further goal to provide an automatic method and device for treating congestive heart failure which uses such a quantitative monitor.

SUMMARY OF THE INVENTION

The invention provides a device and method useful in the diagnosis and treatment of congestive heart failure. Specifically the present invention senses the trans-thoracic impedance as well as patient posture. By correlating changes in posture with trans-thoracic impedance changes, the present invention is able to diagnose and assess the degree of congestive heart failure. The present invention is described in the context of an implantable pulse generator system, but it may also be practiced in conjunction with various types of implantable devices.

BRIEF DESCRIPTION OF THE FIGS.

Figure 4A:
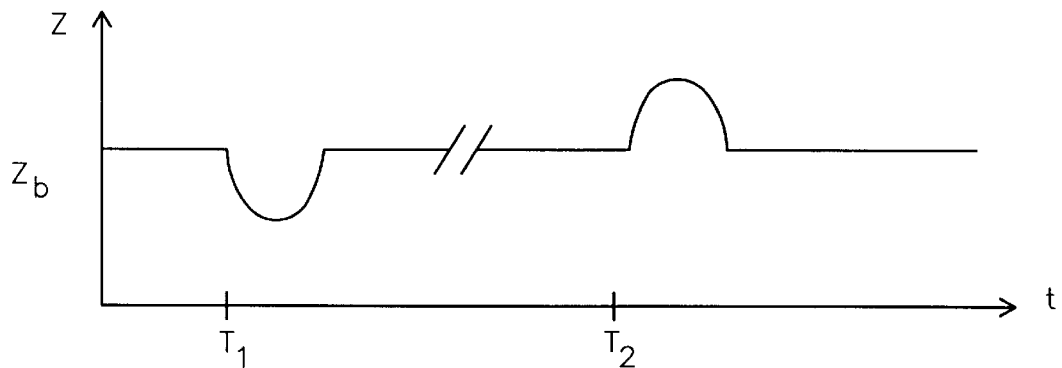

FIGS. 4A, B and C depicts the change in trans-thoracic impedance in three different patients.

Figure 5:
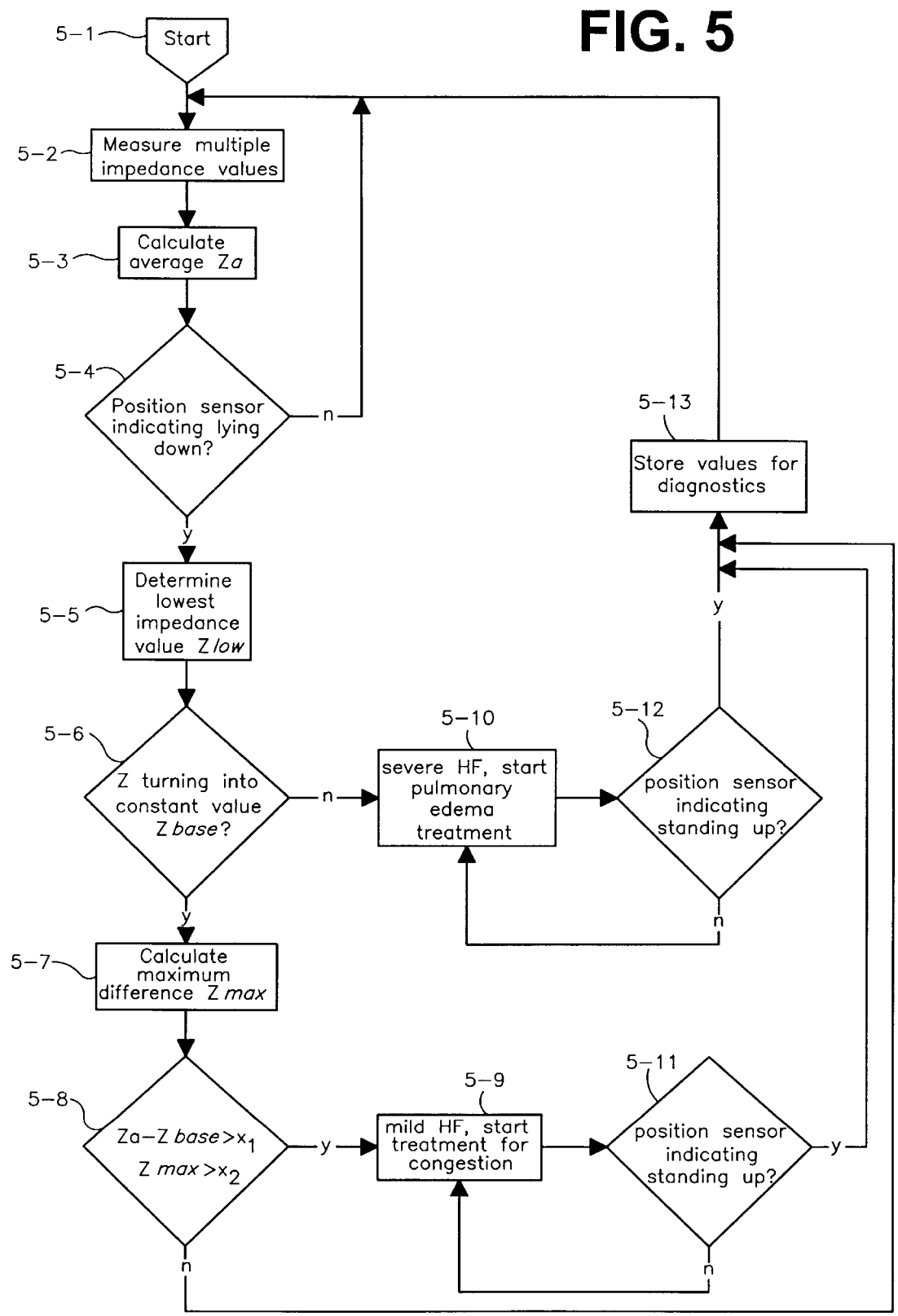

FIG. 5 is a flow chart illustrating the steps used by the present invention to measure the parameters indicative of congestive heart failure, i.e. to measure trans-thoracic impedance and any changes in trans-thoracic impedance subsequent to a change in posture.

Figure 6:
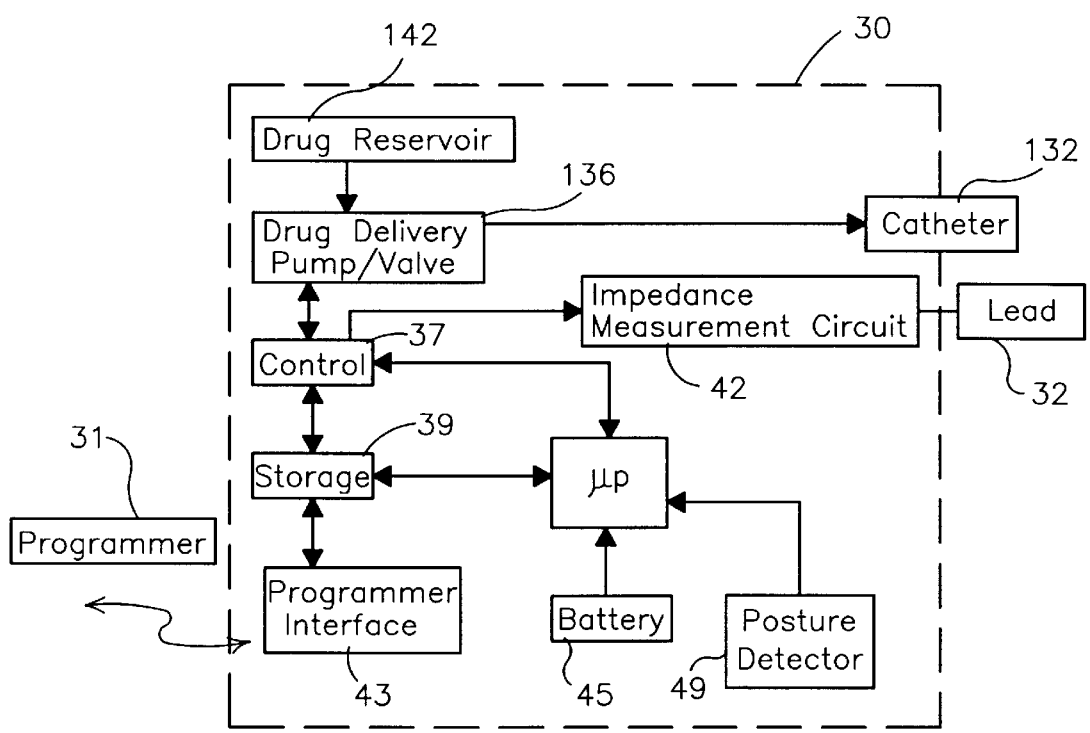

FIG. 6 is shown a block diagram of an alternative embodiment of the invention.

Figure 7:
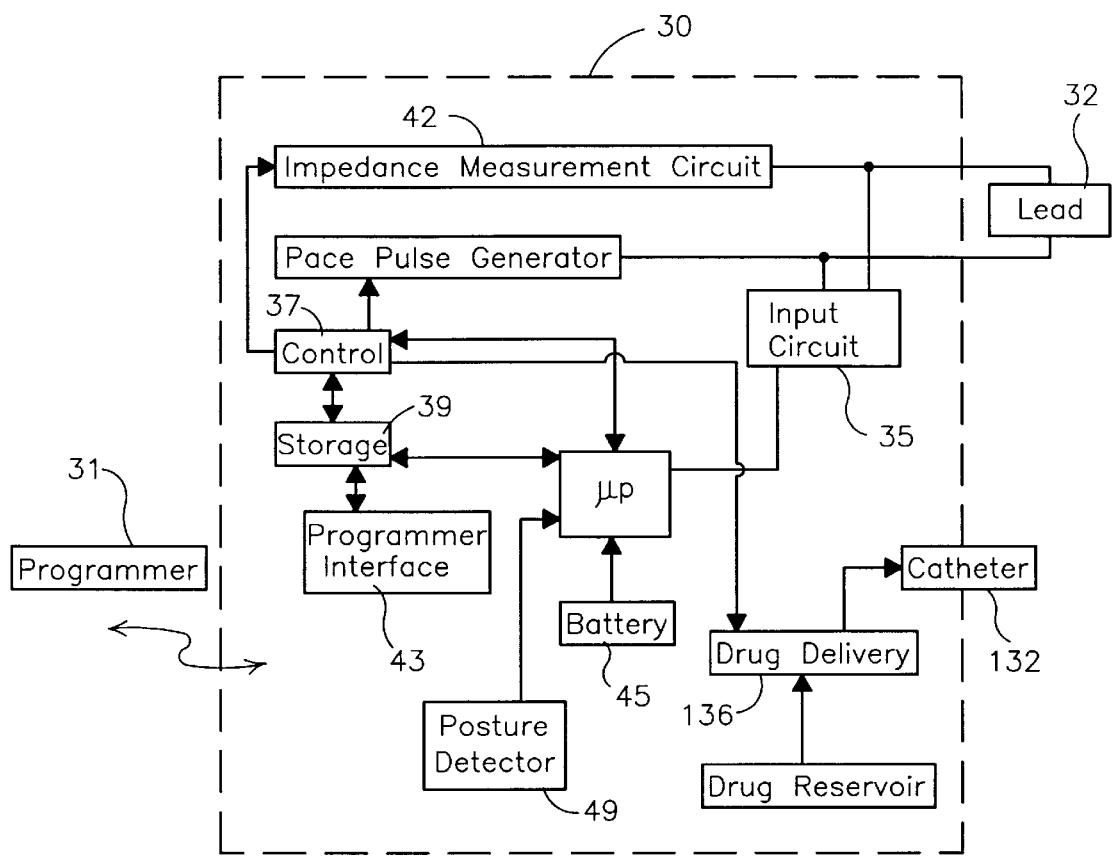

FIG. 7 is a block diagram of a still further alternative embodiment of the invention.

The FIGS are not necessarily to scale.

DETAILED DESCRIPTION OF THE INVENTION

The present invention is based on the physiology of the pulmonary anatomy, and particularly on the fact that the pulmonary circulation is closely related to the cardiac condition. Thus, pulmonary circulation may be used as an indication of cardiac condition, and ultimately heart failure.

In particular, cardiac condition is closely related to right atrial pressure. This is seen in the Frank-Starling law, which describes the relationship between cardiac output and right atrial pressure as a curvilinear function. A sustained increase of hydrostatic pressure in the pulmonary veins, however, indicates a failure of the Frank-Starling Law in the left ventricle.

In patients, this increase of hydrostatic pressure in the pulmonary veins often leads to pulmonary edema in the lower lobes of the lungs. Moreover, as the failure becomes more acute, the pulmonary edema may become more widespread, progressing from the lower lobes of the lungs to the upper lobes.

The present invention uses this physiology to indicate congestive heart failure. In particular the present invention senses trans-thoracic impedance, which is dependent on the blood or fluid content of the lungs, to assist in the detection and quantification of pulmonary edema and thus congestive heart failure.

The present invention, however, uses more than simply the trans-thoracic impedance to quantify pulmonary edema. Trans-thoracic impedance is affected by posture, i.e. whether the subject is lying down or standing up. In a healthy subject, when the subject lies down to sleep, the pulmonary veins are filled up; therefore trans-thoracic impedance will drop for a short period at the onset of the nights. It will quickly thereafter return back up towards its baseline value because the Frank-Startling Law is performing properly and the left ventricular flow out of the lungs increases. In this same healthy subject trans-thoracic impedance will rise briefly at morning (when the subject wakes and stands up) before again returning back down to its baseline value.

In a patient with mild heart failure, however, pulmonary congestion is often present while the patient is lying down. Trans-thoracic impedance will decrease and remain at its lower level throughout the night. At the end of the night trans-thoracic impedance will again return to its base line once the patient rises and is no longer lying down. Impedance will remain at its decreased position in congestive heart failure patients due to the heart's failing Starling mechanism, that is the heart's inadequate ability to pump blood and thus control the hydrostatic pressure in the arteries and veins of the lungs.

In a patient with moderate congestive heart failure, trans-thoracic impedance may continue to decrease throughout the night because of the development of edema and only return to its initial base line reading sometime after the patient has risen.

In a patient with severe congestive heart failure, impedance may remain low due to the persistence of pulmonary edema or congestion.

As mentioned above, the present invention provides a method and device for the diagnosis or treatment of congestive heart failure. Specifically the present invention senses the trans-thoracic impedance as well as patient posture. By correlating changes in posture with trans-thoracic impedance changes, the present invention is able to diagnose and assess the degree of congestive heart failure. Although the present invention shall be described in the context of an implantable pulse generator system, this is only done to illustrate various aspects of the present invention. It is to be understood the present invention may be practiced in conjunction with various types of implantable devices, including, for example defibrillators, cardioverters, heart monitors, drug delivery systems and the like.

Figure 1:
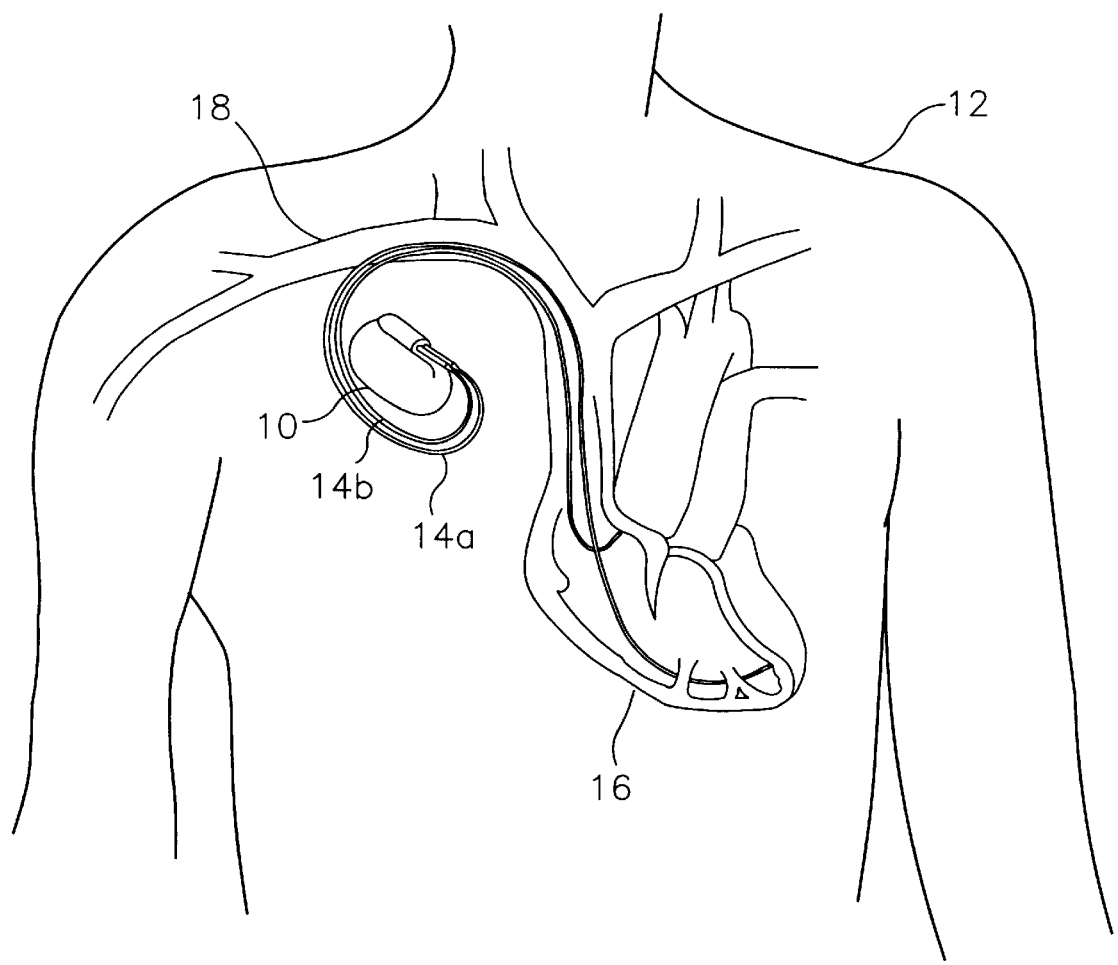
FIG. 1 is a view of a first embodiment of the present invention shown in the context of a device implanted in a patient.

FIG. 1 is a view of a first embodiment of the present invention. As seen, in this embodiment in the invention is shown in the context of a pacemaker 10 implanted in a patient 12. In accordance with conventional practice in the art, pacemaker 10 is housed within a hermetically sealed, biologically inert outer canister, which may itself be conductive and thus serve as an indifferent electrode in the pacemaker's pacing/sensing circuit. One or more pacemaker leads, collectively identified with reference numerals 14a (ventricular) and 14b (atrial) in FIG. 1 are electrically coupled to pacemaker 10 in a conventional manner, extending into the patient's heart 16 via a vein 18. Disposed generally near the distal end of leads 14a and 14b are one or more exposed conductive electrodes for receiving electrical cardiac signals and/or for delivering electrical pacing stimuli to heart 16. As will be appreciated by those of ordinary skill in the art, leads 14a and 14b may be implanted with its distal end situated in either the atrium or ventricle of heart 16. Although two leads are shown here, a so-called "single-pass" lead may also be used, if desired.

Figure 2:
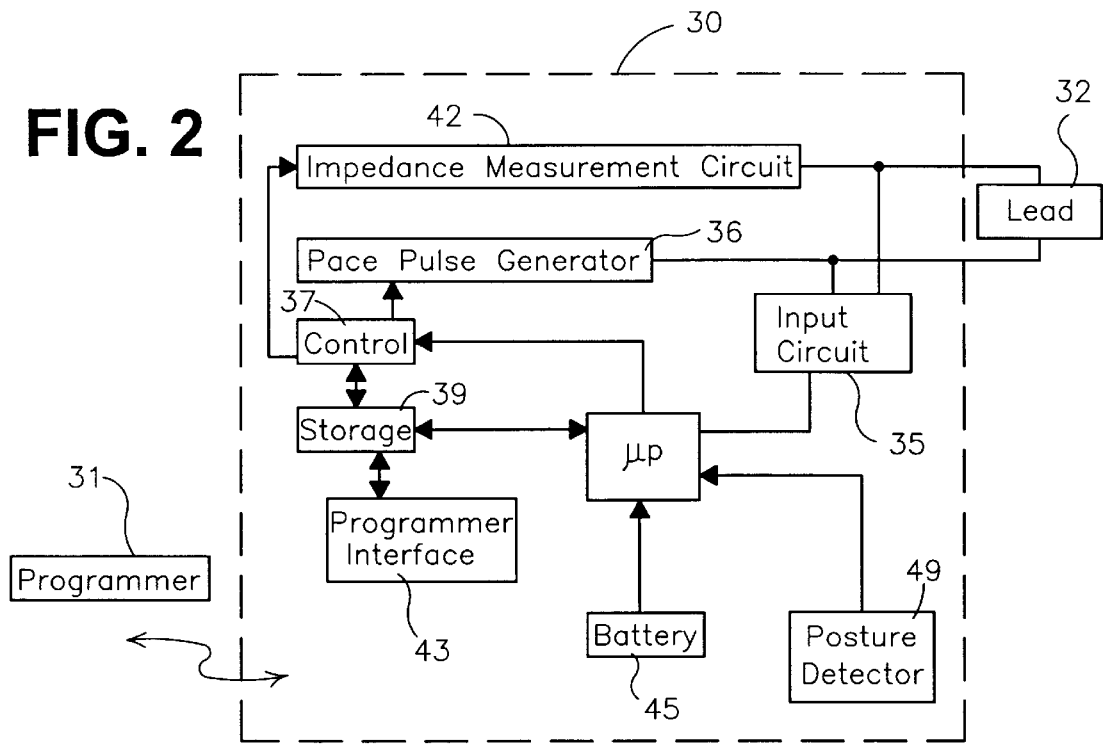
FIG. 2 is a block diagram of the primary functional components of the first embodiment.

Referring now to FIG. 2, there is shown a block diagram of the primary functional components of the system of a preferred embodiment of this invention. The preferred embodiment illustrated comprises an implantable pacemaker 30, an external programmer 31, and a lead 32 for delivering signals between the pacemaker and the patient's heart. The components of the pacemaker illustrated in this figure are only those pertinent to carrying out the subject invention, and it is understood that a functioning implantable pacemaker has a great many different components, as well as stored software, which are not illustrated. See, for example, U.S. Pat. Nos. 5,247,930 and 5,350,411, incorporated herein by reference, illustrating in more detail the primary components of an exemplary implantable pacemaker. The pace pulse generator 36 delivers pace pulses, under influence of control circuitry 37, for delivery through lead 32 to the patient's heart. Control 37 controls pace pulse parameters such as output voltage and pulse duration. In the preferred embodiment these parameters may be set as desired with output voltage set between 1.3–8.0 volts, and pulse widths can be programmed in 25 microsecond steps, within a range of 0.1 ms to 1.0 ms. The impedance measurements are carried out the impedance measurement circuit 42, under control of microprocessor 38 and control 37. Further details regarding the output of this block are discussed below in FIG. 3. Control circuitry 37 acts under the influence of microprocessor 38 and information from storage 39. Storage 39 may be RAM storage associated with the microprocessor (MP) subsystem. Detected signals from the patient's heart are processed in input circuit 35, and forwarded to microprocessor 38 for use in logic and timing determination, in a known manner. As further seen, device also features a posture detector 99 to detect the posture of the patient. As discussed below output form detector is used by the present invention to assess the degree of hear failure. Posture detector 99 may be of any acceptable design, including 2 or 3 axis accelerometers. Examples of posture detectors includes those seen in U.S. Pat. Nos. 5,233,984 and 5,263,491 each of which is incorporated by reference. Programmer 31 communicates with programmer interface block 43, to obtain data which is transferred to storage 39, for use in analyzing system conditions, patient information and changing pacing conditions if warranted. The implantable pacemaker is powered by a battery 45, which supplies electrical power to all of the electrically active components of the pacemaker.

Figure 3:
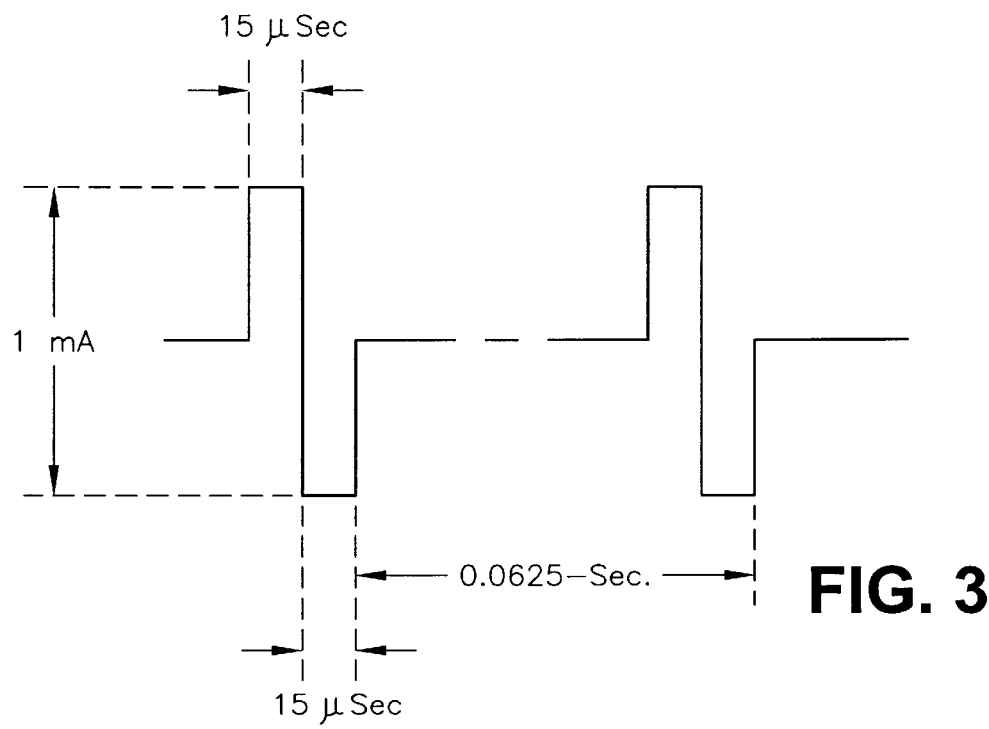
FIG. 3 illustrates an excitation current pulse delivered by the impedance circuitry of the pacemaker shown in FIG. 2.

FIG. 3 illustrates an excitation current pulse delivered by the impedance circuitry of the pacemaker shown in FIG. 2. It is believed a biphasic excitation pulse offers the advantages over a monophasic pulse that the peak amplitude of the excitation pulse is minimized given the overall energy content of the pulse, electrode polarization is canceled, and DC current is balanced to avoid long-term lead metal-ion oxidation. As shown in FIG. 3, each phase of the biphasic pulse lasts for approximately 15-$\mu$Sec, and the pulses are delivered once every 0.0625-Sec (i.e., at a rate of 16-Hz). Preferably impedance is sensed as an average over 60 seconds such that the average impedance values over 2 or 3 breathing cycles is used. In an alternative embodiment, the sensed impedance is further filtered so as to detect coughing by the patient. Such coughing may be used as a further input to quantify and assess the edema and the heart failure as well as the efficacy of any given treatment. One present drawback, however, to the use of coughing as an additional input for heart failure assessment is that presently such patients often take ACE inhibitors, which may themselves induce patients to cough. As future drug therapies are developed, however, drug-induced coughing may not be a problem so the coughing input of the present invention may be of more practical value in the future. Besides analyzing the higher frequency components of the impedance signals, cough may also be detected through a piezoelectric crystal on the device housing or through a lead-based accelerometer on a lead, for example.

FIGS. 4A, B and C depicts the change in trans-thoracic impedance in three different patients. FIG. 4A depicts the change in impedance in over the time from immediately prior to lying down to immediately after awakening and getting up in a normal subject. As seen, at time T1, the start of the night at which time the patient has lied down in order to sleep, the sensed trans-thoracic impedance will decrease. This decrease is seen due to an initial increase in the amount of fluid in the thoracic cavity, especially in and around the lungs. Because the patient has a healthy heart, however, this initial decrease in trans-thoracic impedance will be compensated for by the heart and the trans-thoracic impedance will shortly return back to its baseline value. Similarly at T2, at the end of night when the patient awakens and stands up, trans-thoracic impedance increases as fluid initially drains to the lower extremities. Again, however, because the patient has a healthy heart this initial increase in trans-thoracic impedance will be compensated for by the heart and the trans-thoracic impedance will shortly return back to its baseline value.

Figure 4B:
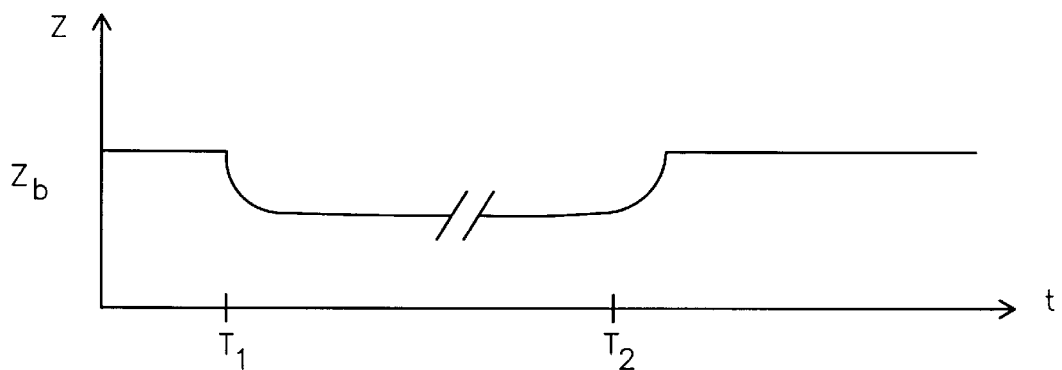

FIG. 4B depicts the change in impedance in over the time from immediately prior to lying down to immediately after awakening and getting up in a subject with a mild degree of heart failure. Like in a healthy subject at time T1 when the patient has lied down in order to sleep, the sensed trans-thoracic impedance will decrease. Because the patient has a mild degree of heart failure, however, the heart is incapable of readily returning the fluid balance in the thoracic cavity to its baseline condition. Thus pulmonary congestion occurs and the initial decrease in trans-thoracic impedance cannot by compensated for by the heart. Thus as seen, over time trans-thoracic impedance remains at a depressed level until the patient rises again at time T2.

Figure 4C:
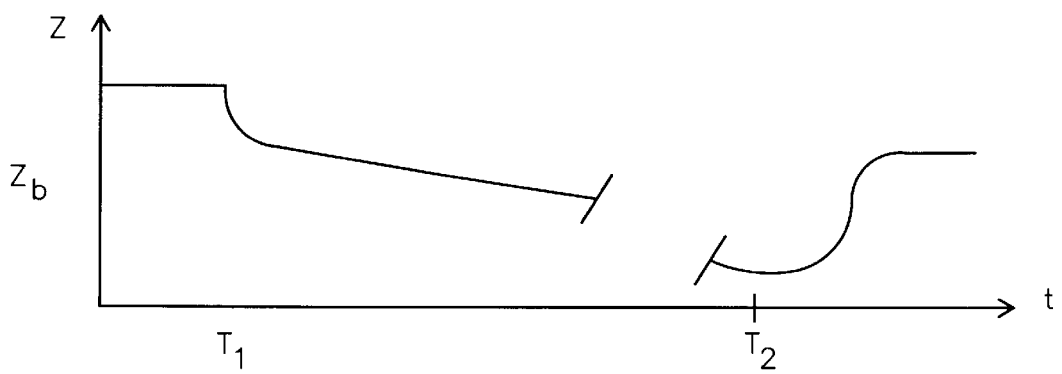

FIG. 4C depicts the change in impedance in over the time from immediately prior to lying down to immediately after awakening and getting up in a subject with a more severe degree of heart failure. As seen, in this patient the initial sensed trans-thoracic impedance decrease does not reach a constant value, but rather continues to drop throughout the night which indicates a continuous increase of fluid and results in pulmonary edema until the patient rises again at time T2.

FIG. 5 is a flow chart illustrating the steps used by the present invention to measure the parameters indicative of congestive heart failure, i.e. to measure trans-thoracic impedance and any changes in trans-thoracic impedance subsequent to a change in posture. As seen, the device starts at block 5-1 and proceeds to block 5-2, where multiple trans-thoracic impedance measurements are taken. These multiple impedance values are measured by giving a small (threshold) excitation current to the tissues found between the tip of the lead and active can of the implantable medical device (best shown in FIG. 1) and measuring the resulting voltage difference. As discussed above, this voltage difference is dependent on the impedance found in the tissues disposed between the electrodes. These impedance measurements should represent the impedance changes caused by fluid changes in the trans-thoracic tissues, especially in the lungs, due to the patient's posture changing. Therefore it is important to either filter or collect several samples and calculate the average, to remove and cardiac or respiratory component from the signal.

As mentioned above, measurements are preferably taken over a series of breathing cycles. In the preferred embodiment an average is collected at a sampling frequency of 16 Hz over 6 seconds, resulting in 96 samples. Preferably, the average used, $Z_A$ is a running average (first in last out). Of course, the particular time over which the samples are collect as well as the frequency at which they are collected may be altered to suit the patient and the desires of the physician.

Next, the device proceeds to block 5-3 where it calculates the average impedance sensed, here designated as trans-thoracic impedance $Z_a$. This value will be used as a baseline value so as to determine whether and with what speed any changes, especially decreases, in trans-thoracic impedance due to postural changes occur.

Next, the device proceeds to block 5-4 and determines whether the posture or position sensor indicates the patient is lying done. If the patient is not lying down the device recycles and proceeds to block 5-2.

If position sensor indicates the patient is lying done, then the device drops down to block 5-5 and determines the lowest impedance value trans-thoracic impedance $Z_{LOW}$. This value is used as a reference to determine if the impedance is continuously decreasing (in patients with severe heart failure), is reaching a steady, but significantly lower baseline (in patients with moderate heart failure) or if the impedance is returning back to the baseline $Z_A$. By storage of the average impedance values at either predetermined times or events, or with the time and posture noted in the data, the physician can get an indication of the progress of the disease (the storage step is seen at block 5-13).

Next, the device proceeds to block 5-6 and determines whether the measured impedance value is turning into a constant baseline value impedance trans-thoracic impedance $Z_{BASE}$. If this is not the case, this is interpreted as a severe degree of congestion that might lead to edema and therapy should be delivered immediately (at block 5-10, until the patient rises again (block 5-12). If the measured impedance is approaching trans-thoracic impedance $Z_{BASE}$ then the device proceeds to block 5-7 where it calculates the maximum impedance difference $Z_{MAX}$. This maximum impedance difference is the difference between the lowest impedance sensed while the patient is lying down compared to the baseline impedance trans-thoracic impedance $Z_{BASE}$. As discussed above, this parameter indicates the degree of fluid which masses in the thoracic region between the sensing electrode due to the patient's posture, i.e. the degree to which the patient has congestive heart failure By this value $Z_{MAX}$ and by comparing the $Z_{BASE}$ value to $Z_A$, the device can determine whether therapy should be delivered. If the difference is larger than x, a moderate degree of heart failure is assumed and a therapy is delivered (block 5-9). Such treatment may include systemic drugs as well as electrical stimulation of the heart or both.

Next, the device proceeds to block 5-8 where a quantification of congestive heart failure is determined. This is accomplished by determining whether the difference between $Z_A$ and $Z_{BASE}$ is greater than a predetermined value $X_1$ (programmed by the physician). In addition, the device may further determine whether $Z_{MAX}$ is greater than a predetermined value $X_2$ (programmed by the physician). Thereafter this information may be used by the device to provide pulmonary edema treatment as shown in block 5-9. Such treatment may include delivery of systemic drugs or localized drugs as well as electrical stimulation of the heart or other areas of the body or any combination or combinations thereof. If such treatments are successful, then the values sensed by the device should move in a direction opposite to that shown in FIGS. 4A, 4B and 4C. That is if a patient with severe HF, with an impedance response as shown in FIG. 4C, receive adequate treatment, the resulting curve might convert to FIG. 4B and patient with moderate HF as in FIG. 4B might convert to FIG. 4A. Of course, if such treatment is nor satisfactory, additional treatments may be further delivered. Thus an important capability of the present invention is that it allows the patient's condition to be assessed and the resulting sensed condition to be feedback into the device so that the most appropriate subsequent therapy may be delivered, both in terms of the time or frequency at which the therapy is delivered, as well as its form, e.g. strength or dosage.

FIG. 6 is shown a block diagram of an alternative embodiment of the invention. In this embodiment illustrated therapy is provided by the delivery of one or more drugs, the drug therapy controlled in part by the sensed impedance and posture changes. As seen, the device is similar to that shown in FIG. 2 with respect to the housing 30, an external programmer 31. Those portions of device not specifically described again should be assumed to operate the same as shown in FIG. 2 Control 37, besides operating as described in FIG. 2, also controls drug delivery components 136 which may include, a pump or valve or both. drug delivery components 136 are further coupled to a drug reservoir 142 as well as a catheter 132 to deliver the drugs to the patient. Preferably this embodiment operates to assess the degree of heart failure as already described above. This embodiment, unlike that shown in FIG. 2 however, has the capability to provide a drug delivery to the patient rather than electrical stimulation.

FIG. 7 is a block diagram of a still further alternative embodiment of the invention. In this embodiment illustrated therapy is provided by the delivery of one or more drugs, the drug therapy controlled in part by the sensed impedance and posture changes, as well as the deliver of electrical stimulation. Preferably this embodiment operates to assess the degree of heart failure as already described above. As seen, in this embodiment the components are essentially a combination of those already described in FIGS. 2 and 6. It must be noted that the selection of drug or stimulation or both to treat the patient in this device is entirely within the control of the patient.

Further, although not shown, the present invention could also be provided as an external device. The cardiac function could be monitored using a Holter-type monitor, the monitor further having a posture sensor. In this way the data would be collected only at night, when the patient rests and awakens. The outputted data could be relayed to the physician/hospital (through telephone transmission) to control and monitor drug doses, i.e., is the dosage sufficient, is the patient taking their drugs. The main advantage of this system is that treatment may be provided as soon as detected, without the need to arrange for the implantation of a medical device and the required follow-up. Moreover, an external device is cheaper than an implantable device.

Moreover, along with trans-thoracic impedance, alternative embodiments may feature additional methods of measuring body parameters, including sensing audible signals indicative of pulmonary congestion or edema, using equipment as disclosed in the patents of Seismed Instruments, Inc., Minneapolis, Minn. In addition, further alternative embodiments may also ultrasonically sense pulmonary edema.

The device, besides monitoring edema and delivering therapy may also be used to control the timings of drug dosages. For example, the device could be programmed so that as soon as the patient lies down and the device diagnosed either pulmonary congestion or even edema a drug can be released from the drug delivery system such as nitrates.

The entire disclosure of each patent and publication cited herein is incorporated by reference, as if each were individually incorporated by reference.

The invention has been described above in connection with particular embodiments and examples, the invention is not necessarily so limited and that numerous other embodiments, examples, uses, modifications and departures from the embodiments, examples and uses are intended to be encompassed by the claims attached hereto. Variations and modifications can be effected within the scope of the following claims. Such modifications may include substituting elements or components which perform substantially the same function in substantially the same way to achieve substantially the same result for those described herein. For example, although shown in the context of an implantable battery powered device, the disclosed invention may also be used in any external device, or any device not directly powered by batteries, e.g. RF powered device or movement powered devices. must be understood the present invention encompasses a much broader scope of embodiments than merely those disclosed herein.

What is claimed is:

1. A device for assessing the degree of heart failure in a patient comprising:

means for sensing the trans thoracic impedance;

means for sensing the posture of the patient; and means for correlating the sensed trans thoracic impedance with the sensed posture to assess the degree of heart failure.

2. The device for assessing the degree of heart failure according to claim 1 wherein the means for sensing the trans-thoracic impedance comprises means for sensing the amount of pulmonary congestion/edema.

3. The device for assessing the degree of heart failure according to claim 2 wherein the means for measuring the trans-thoracic impedance comprises a first electrode adapted to be positioned within a heart of the patient and a second electrode, means for delivering a an excitation current pulse between the first and second electrodes, and means for sensing the impedance in the tissues disposed between the first and second electrodes to the excitation current pulse.

4. The device for assessing the degree of heart failure according to claim 2 wherein the means for sensing the amount of pulmonary congestion/edema comprises means for sensing audible signals indicative of pulmonary congestion/edema.

5. The device for assessing the degree of heart failure according to claim 2 wherein the means for sensing the amount of pulmonary edema comprises ultrasound means for sensing pulmonary edema.

6. The device for assessing the degree of heart failure according to claim 2 wherein the posture sensor comprises an accelerometer.

7. The device for assessing the degree of heart failure according to claim 2 further comprising means for delivering heart failure therapy to the patient.

8. The device for assessing the degree of heart failure according to claim 7 wherein the means for delivering heart failure therapy to the patient comprises feedback means for controlling in time and doses the amount of said delivered heart therapy to the patient in view of the amount of pulmonary congestion/edema sensed.

9. The device for assessing the degree of heart failure according to claim 7 wherein the means for delivering heart failure therapy to the patient comprises means for delivery a drug to the patient.

10. The device for assessing the degree of heart failure according to claim 7 wherein the means for delivering heart failure therapy to the patient comprises means for delivery electrical stimulation to the patient.

11. A device for assessing the degree of heart failure comprising:

means for sensing the trans thoracic impedance over a predetermined period of time;

means for sensing the posture of the patient; and means for correlating the sensed trans thoracic impedance over a predetermined period of time with the sensed posture to assess the degree of heart failure.

12. The device for assessing the degree of heart failure according to claim 11 wherein the means for sensing the trans thoracic impedance over a predetermined period of time comprises averaging the value of a series of trans thoracic impedance values.

13. A method for assessing the degree of heart failure in a patient sing the steps of:

sensing the trans thoracic impedance;

sensing the posture of the patient; and correlating the sensed trans thoracic impedance with the sensed posture to assess the degree of heart failure.

14. The method for assessing the degree of heart failure according to claim 13 wherein the step of sensing the trans-thoracic impedance comprises the step of sensing the amount of pulmonary congestion/edema.

15. The method for assessing the degree of heart failure according to claim 14 wherein the step of sensing the amount of pulmonary congestion/edema comprises the step of sensing audible signals indicative of pulmonary congestion/edema.

16. The method for assessing the degree of heart failure according to claim 14 further comprising the step of delivering heart failure therapy to the patient.

17. The method for assessing the degree of heart failure according to claim 16 wherein the step of delivering heart failure therapy to the patient comprises delivering a drug to the patient.

18. The method for assessing the degree of heart failure according to claim 17 wherein the step of delivering a drug to the patient further comprises the step of controlling in time and the amount of said drug in view of the amount of pulmonary congestion/edema sensed.

19. The method for assessing the degree of heart failure according to claim 14 further comprising the step of delivering electrical stimulation to the patient.

* * * * *

UNITED STATES PATENT AND TRADEMARK OFFICE
CERTIFICATE OF CORRECTION

PATENT NO.     : 6,104,949
DATED          : August 15, 2000
INVENTOR(S)    : Pitts Crick et al.

It is certified that error appears in the above-identified patent and that said Letters Patent is hereby corrected as shown below:

<u>Column 9,</u>
Line 7, change "apatient sing the steps" to -- a patient comprising the steps --.

Signed and Sealed this

Twentieth Day of May, 2003

JAMES E. ROGAN
*Director of the United States Patent and Trademark Office*